United States Patent
Malacoff (10) Patent No.: US 6,540,765 B1
(45) Date of Patent: Apr. 1, 2003

(54) APPARATUS FOR POSITIONING A CARDIAC PACER LEAD

(76) Inventor: Robert F. Malacoff, 1646 County Rd., Bethlehem, PA (US) 18015

( * ) Notice: Subject to any disclaimer, the term of this patent is extended or adjusted under 35 U.S.C. 154(b) by 298 days.

(21) Appl. No.: 09/658,885

(22) Filed: Sep. 11, 2000

(51) Int. Cl.[7] .......................... A61M 25/10; A61N 1/372
(52) U.S. Cl. ........................ 606/194; 600/375; 607/126
(58) Field of Search ................................. 606/194, 192; 600/374, 375, 381; 607/5, 119, 122, 126

(56) References Cited

U.S. PATENT DOCUMENTS

| | | | | |
|---|---|---|---|---|
| 4,581,017 A | * | 4/1986 | Sahota | 606/192 |
| 6,275,730 B1 | * | 8/2001 | KenKnight et al. | 607/5 |
| 6,322,577 B1 | * | 11/2001 | McInnes | 606/194 |

\* cited by examiner

*Primary Examiner*—Peter Nerbun
(74) *Attorney, Agent, or Firm*—Duane Morris LLP (57) ABSTRACT

An apparatus for placing a pacing electrode in the coronary sinus so as to pace the left ventricle of the heart comprises a preshaped, flexible catheter having a distal end and a predetermined shape in an unflexed or steady state condition to facilitate placement of a distal end into the os of the coronary sinus within the right atrium of the heart. The catheter includes a first lumen which extends from an entry port at the proximal end of the catheter end of the catheter, through the catheter and terminating at an exit port at the distal end of the catheter. The catheter also includes a second lumen which extends from a first port in the vicinity of the proximal end of the catheter through the catheter and terminating at a second port which is in fluid communication with an inflatable/deflatable balloon in the vicinity of the distal end of the catheter. An inflating/deflating device, such as a syringe, is attachable to the first port of the second lumen of the catheter, for inflating/deflating the balloon. At least one port, extending through an outer wall of the catheter on the distal side of the balloon, is in fluid communication with at one port disposed through the outer wall of the catheter on the proximal side of the balloon. The apparatus also includes a pacing lead with over-the-wire capability which is removably insertable through the first lumen of the catheter.

10 Claims, 7 Drawing Sheets

APPARATUS FOR POSITIONING A CARDIAC PACER LEAD

BACKGROUND OF THE INVENTION

This invention pertains to catheters and more particularly to an apparatus for placing cardiac pacing leads.

Cardiac pacing leads are used in conjunction with cardiac pacemakers to apply electrical stimuli to the heart causing the heart muscle to contract. This type of stimulation, or pacing, is used in cases where problems occur in the intrinsic electrical system of the heart.

In the past, pacing electrodes were introduced into the right atrium and/or right ventricle of the heart by means of a catheter inserted in the left subclavian vein (or directly via the cephalic vein) through the superior vena cava into the right atrium across the tricuspid valve into the right ventricle. In those cases where it is desirable to apply an electrical pacing pulse to the ventricle only, the pacing electrode is secured to the endocardium or inner lining of the right ventricle. In those cases where coordinated A-V pacing is desired, a second pacing electrode is secured to the inner lining of the right atrium.

In some cases, it is desirable to secure a pacing lead in the coronary sinus whereby an electrical pacing pulse is transmitted to the left ventricle to improve the pumping action of the heart. However, such a procedure has herefore been extremely difficult using traditional catheterization techniques. This is because of several factors including the inconsistency of the location of the Os of the coronary sinus. Also, the heart is in motion, contracting 60 to 100 times a minute. In addition, the course of the coronary sinus beyond the Os may be quite variable. Furthermore, visualization of the course of the coronary sinus and its multiple branches has been suboptimal. Also, passage of the pacing electrode has been hampered by the anatomy of the coronary sinus and its branches as well as a lack of a mechanically stable delivery system that will allow real-time coronary sinus venography during pacing electrode placement.

SUMMARY OF THE INVENTION

The present invention comprises an apparatus for placing a pacing electrode in the coronary sinus so as to pace the left ventricle of the heart. This apparatus comprises a preshaped, flexible catheter having a distal end and a predetermined shape in an unflexed or steady state condition to facilitate placement of the distal end into the os of the coronory sinus within the right atrium of the heart. This predetermined shape is imparted to the catheter using a material which, while flexible, imparts a structural memory such that the catheter retains its predetermined shape in its unflexed or steady state condition. The catheter includes a first lumen which extends from an entry port at a proximal end of the catheter through the catheter terminating at an exit port at the distal end of the catheter. The catheter includes a second lumen which extends from a first port in the vicinity of the proximal end of the catheter through the catheter terminating at a second port which is in fluid communication with an inflatable/deflatable balloon in the vicinity of the distal end of the catheter. An inflating/deflating device, such as a syringe, is attachable to the first port of the second lumen, for inflating/deflating the balloon. At least one port, disposed through an outer wall of the catheter on a distal side of the balloon, is in fluid communication with at least one port disposed through the outer wall of the catheter on a proximal side of the balloon. The apparatus also includes a pacing lead with over-the-wire capability which is removably insertable through the first lumen of the catheter.

DETAILED DESCRIPTION

Figure 1:
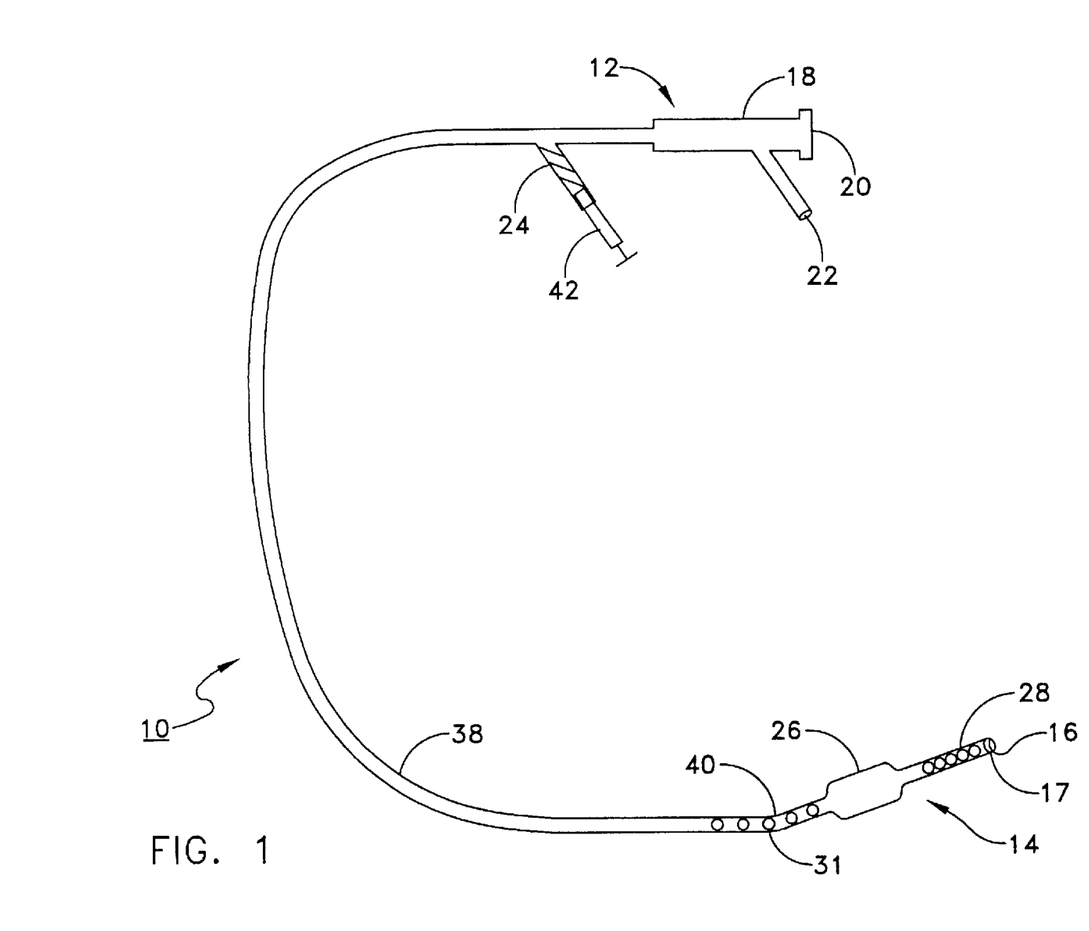
FIG. 1 is a diagram of a catheter portion the apparatus of the present invention, generally depicting the predetermined shape formed in the catheter in its unflexed or steady state.

Referring to FIG. 1, there is depicted a catheter portion of the apparatus for placing a pacing electrode of the present invention, generally designated 10. The preferred size of catheter 10 is 8 or 9 French. The catheter 10 has a proximal end 12 and a distal end 14. A first lumen 16 extends through the catheter from the proximal end 12 to the distal end 14. terminating in an exit port 17. A multiport adaptor, commonly referred to as a Tuohy-Borst adaptor 18 is connected to the proximal end 12 of the catheter 10. The Tuohy-Borst adaptor 18 includes a first port 20 and a second port 22.

Figure 5:
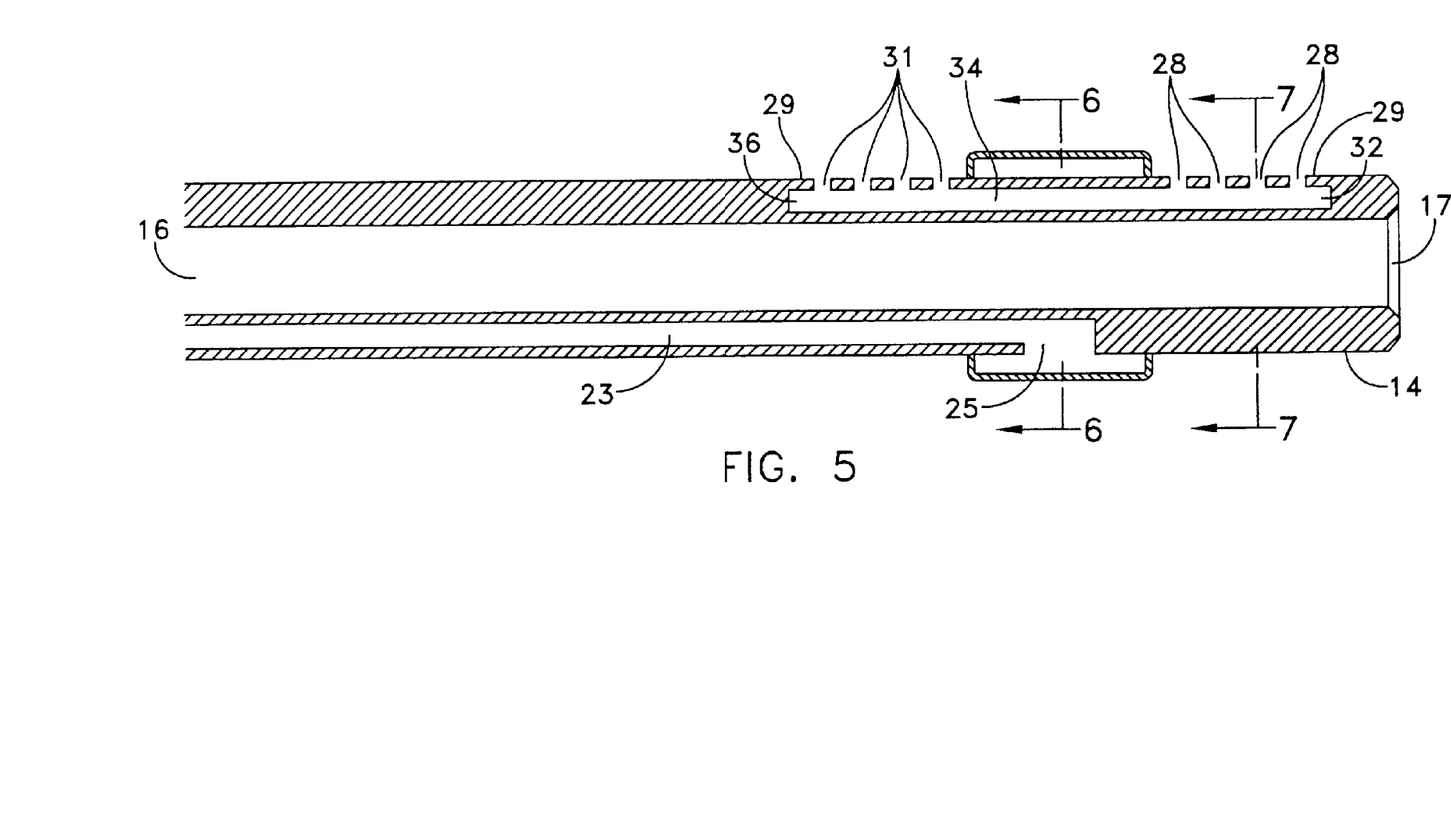
FIG. 5 is a longitudinal cross-section of an alternate embodiment of the distal segment of the catheter portion of the apparatus of the present invention.

The catheter 10 includes a second lumen 23 (see FIGS. 5 and 8) which extends within the catheter 10 from a first port 24, positioned in the vicinity of the proximal end 12 of the catheter 10 to a second port 25 positioned in the vicinity of the distal end 14 of catheter 10 (see FIG. 5) zin fluid communication with an inflatable/deflatable balloon 26 disposed around the periphery of the catheter 10 in the vicinity of the distal end 14. The balloon preferably has a longitudinal dimension of 10—15 mm. At least one perfusion port, disposed through an outer wall of the catheter on a distal side of the balloon, is in fluid communication with at least one port disposed through the outer wall of the catheter on a proximal side of the balloon. In the embodiment depicted in FIGS. 1, 5 and 8, a first group of perfusion ports 28 is disposed in an outer wall 29 of the catheter 10 on the distal side of the balloon 26, and a second group of perfusion ports 31 is disposed in the outer wall 29 of the catheter 10 on the proximal side of the balloon 26. Although each of the first 28 and second 31 groups is depicted having four ports, each group may have more or less ports and such is within the scope and contemplation of the present invention.

Figure 6:
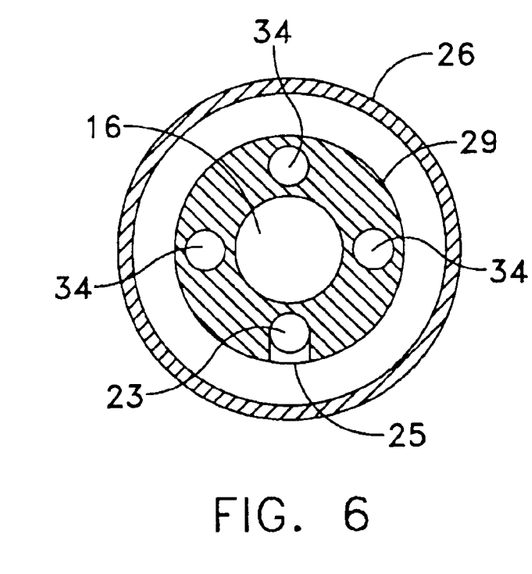
FIG. 6 is a lateral cross-section of the distal segment of the catheter portion of the apparatus of the present invention taken along lines 6—6 of FIG. 5.
Figure 7:
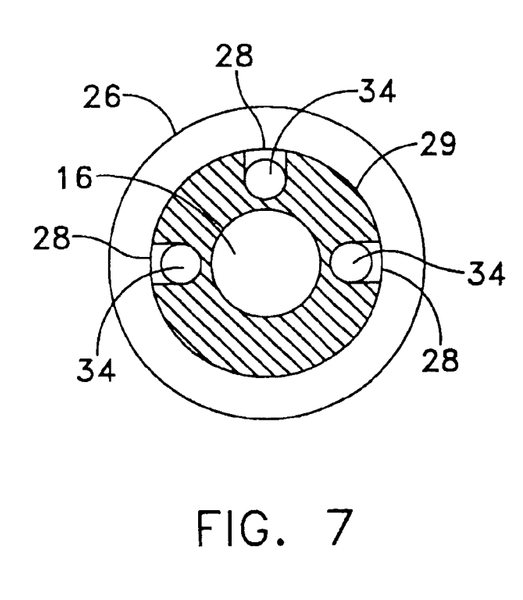
FIG. 7 is a lateral cross-section of the distal segment of the catheter portion of the apparatus of the present invention taken along lines 7—7 of FIG. 5.
Figure 8:
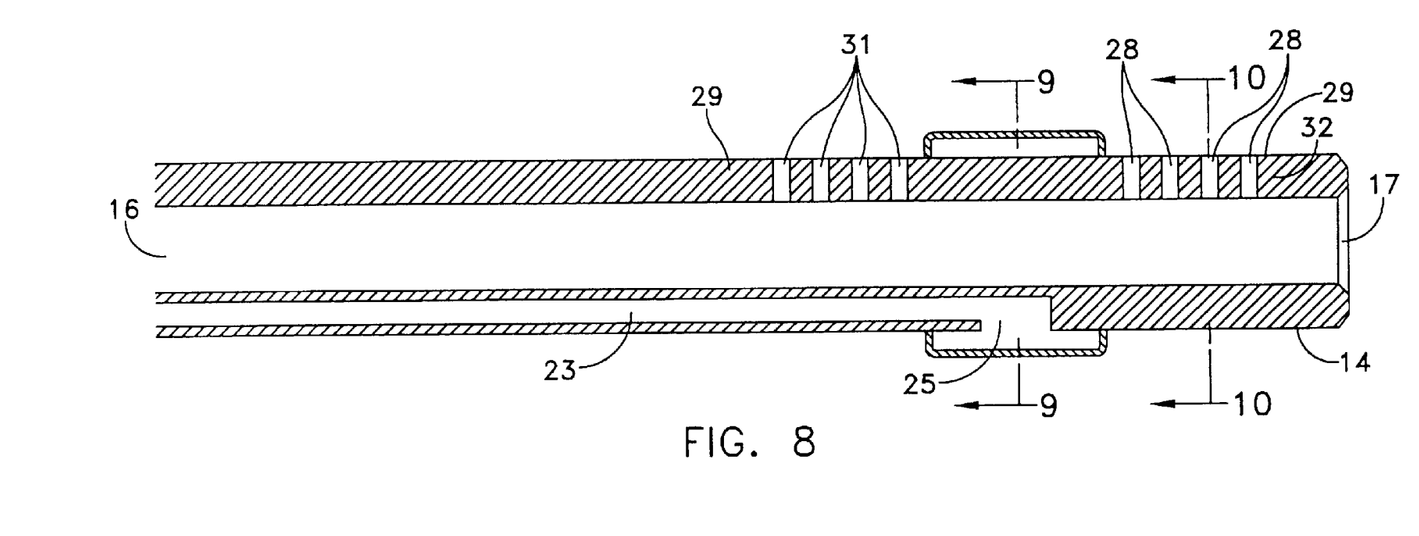
FIG. 8 is a longitudinal cross-section of an embodiment of the distal segment of the catheter portion of the apparatus of the present invention.
Figure 9:
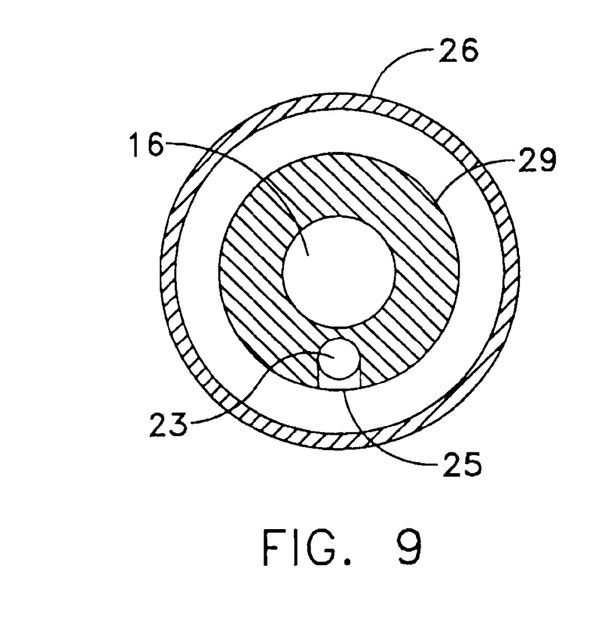
FIG. 9 is a lateral cross-section of the distal segment of the catheter portion of the apparatus of the present invention taken along lines 9—9 of FIG. 8.
Figure 10:
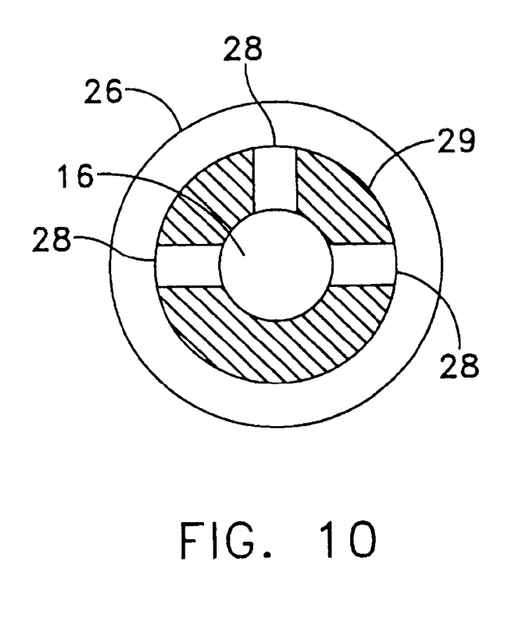
FIG. 10 is a lateral cross-section of the distal segment of the catheter portion of the apparatus of the present invention taken along lines 10—10 of FIG. 8.

As shown in the embodiment depicted in FIG. 8, the perfusion ports of the first 28 and second 31 groups extend through the outer wall 29 of the catheter 10 to the first lumen 16 thereby establishing fluid communication between :the environment outside the outer wall 29 of the catheter 10 and the first lumen 16. The first lumen 16 provides a conduit for fluid communication between the first 28 and second 31 groups of perfusion ports. In the embodiment depicted in FIGS. 9 and 10, there are three sets of groups of perfusion ports positioned around the periphery of the catheter 10, although there may be more or less sets of groups disposed around at least a portion of the periphery, and such is within the scope and contemplation of the present invention and such is within the scope and contemplation of the present invention. As shown in the alternate embodiment depicted in FIG. 5, a distal end 32 of a fluid conduit 34 is in fluid communication with the first group of perfusion ports 28; and a proximal end 36 of the fluid conduit 34 is in fluid communication with the second group of perfusion ports 31. In the embodiment depicted in FIGS. 6 and 7, there are three sets of first groups of perfusion ports 28 positioned around the periphery of the catheter 10 each having a fluid conduit 34 in fluid communication therewith, each of which is in fluid communication with a respective set of second groups of perfusion ports (not shown). Although there are three sets of first 28 and second 31 groups of perfusion ports positioned around the periphery, there may be more or less disposed around at least a portion of the periphery and such is within the scope and contemplation of the present invention.

As shown in FIG. 1, the catheter 10 has a predetermined shape having a primary angle 38 and a secondary angle 40. This predetermined shape facilitates placement of the distal end 14 of the catheter 10 into the Os of the coronary sinus. The catheter 10 is preferably preshaped using a material which, while flexible, imparts a structural memory such that the catheter retains its predetermined shape in its unflexed or steady state condition. It is preferred that this predetermined configuration be made in multiple sizes, for example, small, medium, and large. Since it is the function of the predetermined shape to facilitate placement of the distal end 14 of the catheter 10 into the os of the coronary sinus, the size utilized (i.e. small, medium or large) will be determined by the anatomy of the heart of the particular patient. It is believed that three sizes, small, medium and large, of the predetermined shape will accommodate substantially all variations in the anatomy of hearts typically encountered.

Figure 2:
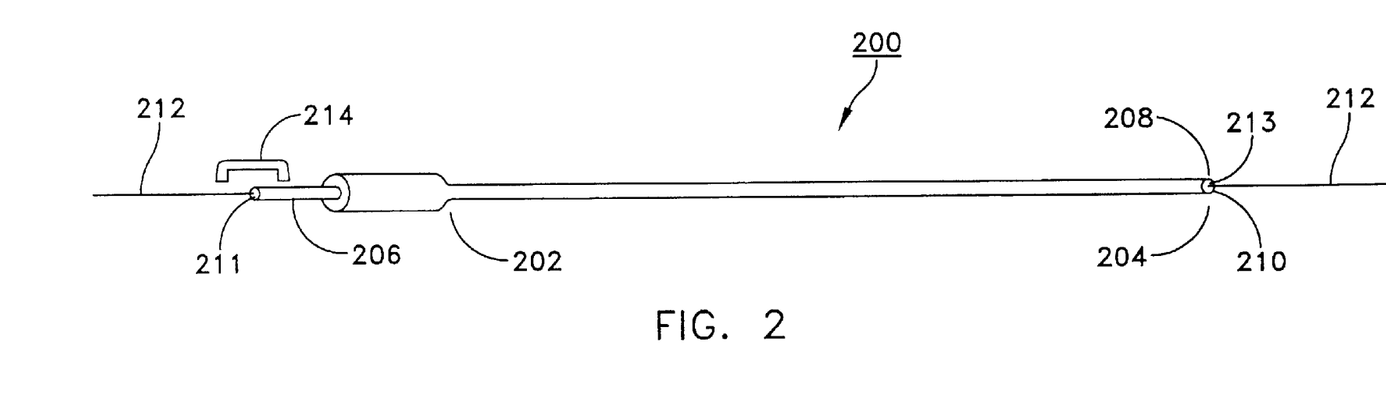
FIG. 2 is a diagram of a pacing lead with over-the-wire capability for use in connection with the apparatus of the present invention.

Referring now to FIG. 2, there is shown:a pacing lead, generally referred to as 200. The pacing lead 200 comprises a proximal end 202 and a distal end 204. A terminal electrode, 206, is disposed at the proximal end 202 of the pacing lead 200. A pacing electrode 208 is disposed at the distal end 204 of the pacing lead 200. An electrical conductor (not shown) electrically connects the terminal electrode 206 to the pacing electrode 208.

The pacing lead 200 contains a lumen 210 which extends between an entry port 211 at the proximal end 202 and an exit port 213 at the distal end 204 of the pacing lead 200. A wire guide 212 is removably insertable through the entry port 211, the lumen 210 and the exit port 213 of the pacing lead 200. A locking mechanism, such as a clip 214, is used to lock the wire guide 212 in place with respect to the pacing lead 200.

Figures 3, 4:
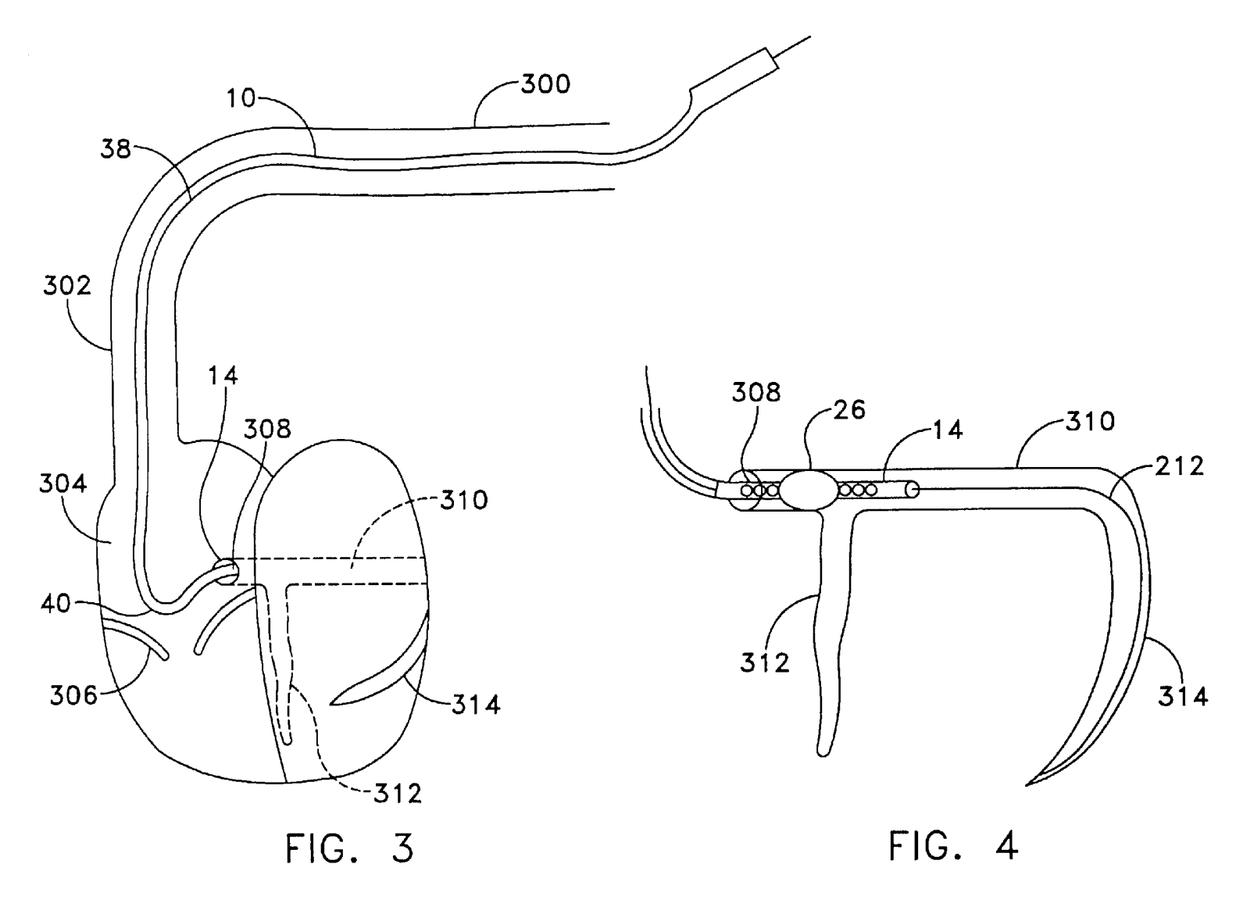
FIG. 3 is a schematic representation of a human heart and coronary sinus depicting placement of a distal segment of the catheter portion of the present invention into the os of the coronary sinus.
FIG. 4 is a schematic representation of the coronary sinus of a human heart depicting placement of a pacing lead in the coronary sinus in accordance with the present invention.

The apparatus of the present invention is used to insert a pacing lead into the coronary sinus of the heart as follows. Referring to FIG. 3, the catheter 10 is inserted percutaneously into the left subclavian vein 300 through the superior vena cava 302 into the right atrium 304. As stated above, the catheter 10 has a predetermined shape which facilitates placement, with the primary angle 38 and the secondary angle 40 aiding the positioning of the distal end 14 of the catheter 10 within the right atrium 304 above the tricuspid valve 306 and into the os or opening 308 of the coronary sinus 310. This predetermined shape is imparted to the catheter 10 using a material which is flexible and which imparts a structural memory such that the catheter retains its predetermined shape in its unflexed or steady state condition.

Once the distal end 14 of the catheter 10 is inserted into the coronary sinus 310, with the exit port 17 preferably positioned past the inferior branch 312 of the coronory sinus 310 as shown, for example in FIG. 4, the balloon 26 is inflated using an inflating/deflating device, such as a balloon syringe 42 (see FIG. 1). This secures and stabilizes the distal end 14 of the catheter 10 within the coronary sinus 310. As previously stated, at least one first group of perfusion ports 28 (comprising at least one perfusion port) on the distal side of the balloon 26 is in fluid communication with at least one second group of perfusion ports 31 (comprising at least one perfusion port) on the proximal side of the balloon 26 via the first lumen 16 (see embodiment depicted in FIGS. 8–10) or via a fluid conduit 34 (see FIGS. 5–7). This arrangement enables the blood in the coronary sinus 310 to flow into the perfusion ports 28, through the first lumen 16 or fluid conduit 34 (depending on the embodiment used), past the inflated balloon 26, out of the perfusion ports 31and into the right atrium thereby minimizing the possibility that the distal end of the catheter 10 will be forced out of the coronary sinus by motion of the beating heart and the force of the blood flow, and also minimizing obstruction of the blood flow caused by the inflated balloon.

Once the distal end 14 of the catheter 10 has been secured and stabilized within the coronary sinus 310 as described above, an angiogram may be performed by injecting dye into the second port 22 of the Tuohy-Borst adaptor 18. The dye travels through the first lumen 16 and into the coronary sinus 310 through the exit port 17 at the distal end 14 of the catheter 10. The pacing lead 200, having the wire guide 212 disposed therein, is inserted into the first port 20 of the Tuohy-Borst adaptor 18 and advanced through the first lumen 16 of the catheter 20 to the primary angle 38. The wire guide 212 is then advanced into the coronary sinus 310, as shown, for example, in FIG. 4, and placed in a lateral branch 314 of the coronary sinus 310 using periodic angiography as required to assist in the placement.

At this point, the stabilizing balloon 26 may be deflated or may remain inflated as circumstances dictate. Once the distal end of the wire guide 212 is correctly positioned in the lateral branch, the stabilizing balloon 26 is reinflated, if previously deflated, and the pacing lead 200 is advanced over the wire guide 212 to the destination location. The stabilizing balloon 26 is then deflated and the catheter 10 is withdrawn. During catheter withdrawal, the wire guide 212 is locked to the pacing lead 200 using the locking mechanism 214. Once the catheter 10 is removed, the pacing lead 200 is unlocked from the wire guide 212 and the wire guide 212 is removed leaving the pacing lead 200 in place with the pacing electrode 208 disposed in a lateral branch 314 of the coronary sinus 310. Pacing at this point will capture and thereby pace the left ventricle. Once the pacing electrode 208 has been placed in position in a lateral branch 314 of the coronary sinus 310, as described above, the terminal electrode 206 of the pacing lead 200 is electrically connected to a pacemaker as is known in the art whereby pacing of the left ventricle can be initiated.

I claim:

1. An apparatus for enabling placement of a pacing electrode in the coronary sinus of a heart to facilitate pacing of the left ventricle, said apparatus comprising:

a) a flexible catheter having a distal end and a predetermined shape in an unflexed state to facilitate placement of said distal end into the os of the coronery sinus within the right atrium of the heart;

b) a first lumen extending through said catheter from an entry port at a proximal end to an exit port at said distal end;

c) a second lumen extending through said catheter from a first port disposed in said catheter in the vicinity of said proximal end and terminating at a second port which is in fluid communication with an inflatable/deflatable balloon disposed around the periphery of said catheter in the vicinity of said distal end; and d) at least one first port, disposed through an outer wall of said catheter on a distal side of said balloon which is in fluid communication with at least one second port, disposed through an outer wall of said catheter on a proximal side of said balloon.

2. The apparatus in accordance with claim 1 wherein said catheter includes a plurality of first ports disposed through the outer wall of said catheter around at least a portion of the periphery of said catheter on the distal side of said balloon and a plurality of second ports disposed through the outer wall of said catheter around at least a portion of the periphery of said catheter on the proximal side of said balloon.

3. The apparatus in accordance with claim 1 additionally comprising a multiport adapter having an insertion port coupled to said entry port and a second port in fluid communication with said entry port.

4. The apparatus in accordance with claim 3 wherein a balloon inflating/deflating device is attached to the first port of said second lumen.

5. The apparatus in accordance with claim 4 wherein said balloon inflating/deflating device comprises a balloon syringe.

6. The apparatus in accordance with claim 1 additionally comprising a pacing lead insertable into the entry port of said catheter, through the first lumen of said catheter and out of the exit port of said catheter.

7. The apparatus in accordance with claim 6 wherein said pacing lead includes a lumen which extends between an entry port and an exit port, and a wire guide which is removably insertable into the pacing lead entry port, through the pacing lead lumen and out of the pacing lead exit port.

8. The apparatus in accordance with claim 1 wherein said predetermined shape includes a primary angle and a secondary angle.

9. The apparatus in accordance with claim 1 wherein said catheter includes at least one first group of ports disposed through the outer wall of said catheter on the distal side of said balloon which is in fluid communication with at least one second group of ports disposed through the outer wall of said catheter on the proximal side of said balloon.

10. The apparatus in accordance with claim 9 wherein said catheter includes a plurality of said first and second groups of ports disposed around at least a portion of the periphery of said catheter.

* * * * *